(12) United States Patent
Russo

(10) Patent No.: US 8,636,699 B2
(45) Date of Patent: Jan. 28, 2014

(54) PERCUTANEOUS CATHETER ANCHORING DEVICE

(75) Inventor: Ronald D. Russo, Naples, FL (US)

(73) Assignee: Dale Medical Products, Inc., Plainville, MA (US)

(*) Notice: Subject to any disclaimer, the term of this patent is extended or adjusted under 35 U.S.C. 154(b) by 24 days.

(21) Appl. No.: 13/408,036

(22) Filed: Feb. 29, 2012

(65) Prior Publication Data
US 2012/0226237 A1 Sep. 6, 2012

Related U.S. Application Data

(60) Provisional application No. 61/448,261, filed on Mar. 2, 2011.

(51) Int. Cl.
A61M 5/32 (2006.01)

(52) U.S. Cl.
USPC ........................................ 604/174; 604/177

(58) Field of Classification Search
USPC ................ 604/174, 177–180; 128/DIG. 6, 15
See application file for complete search history.

(56) References Cited

U.S. PATENT DOCUMENTS

| 3,146,778 | A | * | 9/1964 | Krawiec | 604/180 |
|---|---|---|---|---|---|
| 4,838,867 | A | * | 6/1989 | Kalt et al. | 604/180 |
| 4,854,015 | A | * | 8/1989 | Shaull | 24/16 R |
| 5,098,399 | A | * | 3/1992 | Tollini | 604/180 |
| 5,147,322 | A | * | 9/1992 | Bowen et al. | 604/180 |
| 5,292,312 | A | * | 3/1994 | Delk et al. | 604/180 |
| 5,352,209 | A | * | 10/1994 | Bird et al. | 604/179 |
| 5,449,340 | A | * | 9/1995 | Tollini | 602/58 |
| 5,664,581 | A | * | 9/1997 | Ashley | 128/876 |
| 5,879,335 | A | * | 3/1999 | Martinez et al. | 604/179 |
| 5,941,856 | A | * | 8/1999 | Kovacs et al. | 604/179 |
| 6,317,933 | B1 | * | 11/2001 | Suenaga | 24/16 R |
| 6,419,660 | B1 | * | 7/2002 | Russo | 604/180 |
| 7,284,730 | B2 | * | 10/2007 | Walsh et al. | 248/74.3 |
| 7,624,480 | B2 | * | 12/2009 | Coronel | 24/306 |
| 2008/0108947 | A1 | * | 5/2008 | Crawford | 604/174 |

* cited by examiner

Primary Examiner — Nicholas Lucchesi
Assistant Examiner — Rebecca E Eisenberg
(74) Attorney, Agent, or Firm — Finnegan, Henderson, Farabow, Garrett & Dunner, LLP

(57) ABSTRACT

The present disclosure provide catheter anchoring devices including anchoring devices that can be used to secure percutaneous catheters to a patient. In some embodiments, a catheter anchoring device comprises a locking tab having a front surface including a first mechanical engagement material and a back surface to be adhesively secured to a catheter by wrapping the back surface around a catheter surface. The catheter anchoring device further comprises a base portion comprising a base material layer including a bottom surface for adhesive application to the skin of a patient and a top surface including a second mechanical engagement material for engagement with the first mechanical engagement material of the locking tab; and a flexible closure extending from the base material layer and including a third mechanical engagement material for engagement with the top surface of the base material layer and a through-hole sized to allow passage of a tab protrusion.

21 Claims, 8 Drawing Sheets

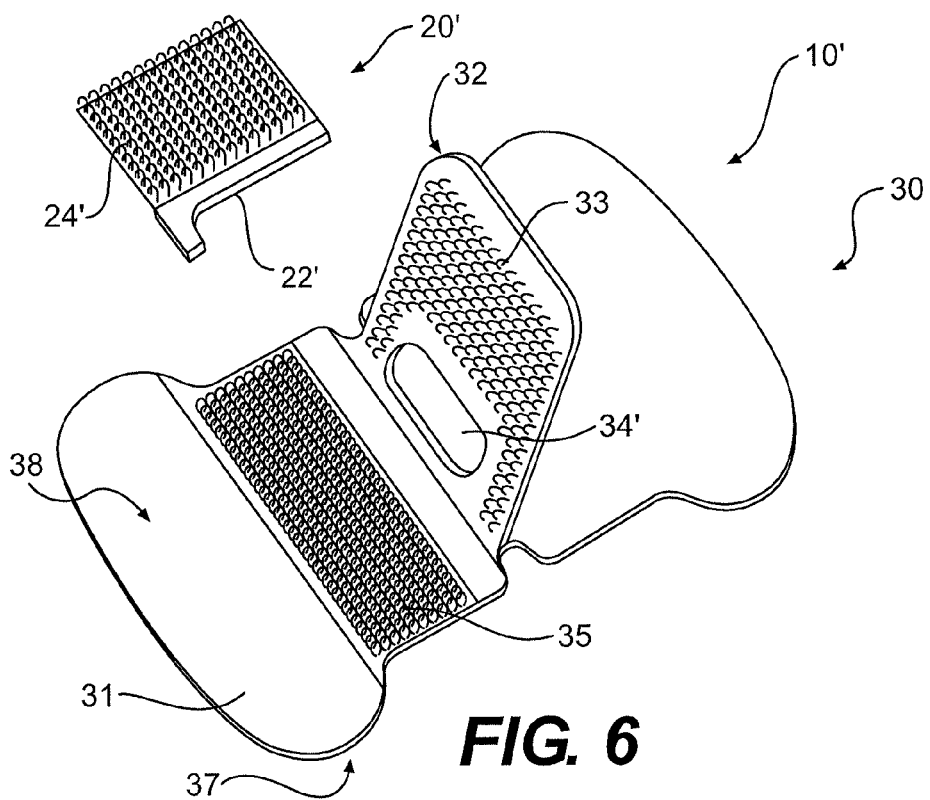
FIG. 6
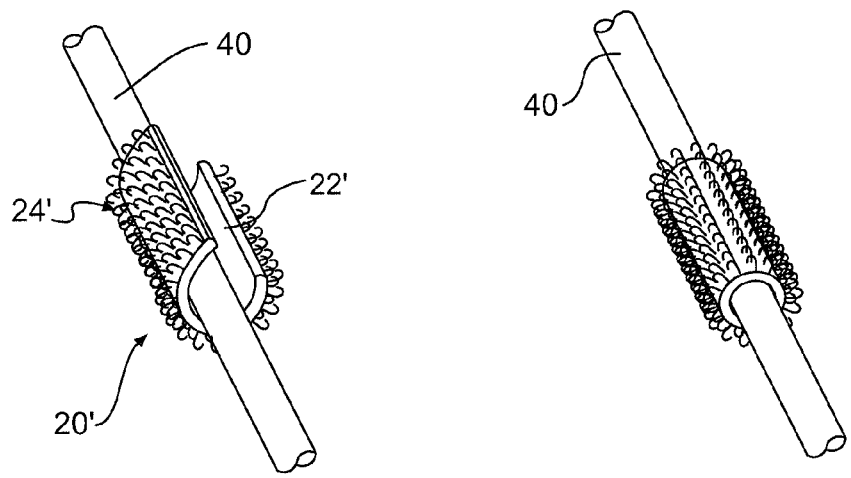
FIG. 7A  FIG. 7B

PERCUTANEOUS CATHETER ANCHORING DEVICE

PRIORITY

This application claims priority under 35 U.S.C. §119 to U.S. Provisional Patent Application No. 61/448,261, filed on Mar. 2, 2011, which is herein incorporated in its entirety by reference.

TECHNICAL FILED

The present disclosure relates to medical anchoring devices, and more particularly, to a catheter anchoring device.

BACKGROUND

The present disclosure relates to catheter fixation or anchoring devices that can securely fixate a wide variety of catheters. The devices can be used for through-the-skin (percutaneous) catheters. Such catheters include, for example, dialysis catheters, interventional radiological catheters, percutaneous endoscopic gastrostomy tubes, and nephrostomy catheters.

Percutaneous catheters are generally placed by interventional radiologists or endoscopic surgeons and can be used, for example, to drain an internal organ abscess or to infuse medication. These catheters are placed directly through the skin and may be left in place for several weeks or months. Typically, they have some sort of external bolster on the skin exit site and are flexed at a sharp angle to lay flat along the skin. The proximal end of the catheter typically has an adapter for connection to a drainage set or to a liquid medication delivery system such as an intravenous administration set.

In many cases, it may be difficult to secure the catheters in place to prevent them from moving out of the required anatomic position. For example, these catheters are generally made from either polyurethane or silicone, which may not easily adhere to other materials and cannot be reliably secured with available devices. In addition, there is a need for catheter anchoring devices that can be used to secure percutaneous catheters having a range of sizes.

SUMMARY

In one embodiment, a catheter anchoring device is provided. The device can comprise a locking tab having a front surface including a hook or loop type material and a back surface containing an adhesive. The locking tab can have a size and dimensions such that the back surface of the tab can be adhesively secured to a catheter by wrapping the back surface around a catheter surface such that that the locking tab forms an outwardly extending protrusion from the catheter. The device can also include a base portion. The base portion can include a base material layer including a bottom surface for adhesive application to the skin of a patient and a top surface including either a hook or loop type material for engagement with the hook or loop type material of the locking tab. The base portion can also include a flexible closure extending from the base material layer and including a hook or loop type material for engagement with the top surface of the base material layer and a through-hole sized to allow passage of the tab protrusion when the tab is secured to a catheter to form an interlocking engagement with the closure when the closure is engaged with the top surface of the base portion.

In another embodiment, a second catheter anchoring device is provided. The device can include a locking tab having a front surface including either or hook or loop type material and a back surface containing an adhesive. The device can also include a base portion comprising a base material layer including a bottom surface for adhesive application to the skin of a patient and a top surface including either a hook or loop type material for engagement with the hook or loop type material of the locking tab. The device can also include a flexible closure extending from the base material layer and including a hook or loop type material for engagement with the top surface of the base material layer and an elongated opening sized to allow at least a portion of the locking tab to protrude through the opening when the tab is wrapped around a catheter body and secured to the top surface of the base material layer.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 6 is a perspective view of another embodiment of the anchoring device of the present disclosure.

FIG. 7A is a perspective view of an adhesive locking tab of the device of FIG. 6 being attached to a catheter.

FIG. 7B is a perspective view of an adhesive locking tab of the device of FIG. 6 attached to a catheter.

DESCRIPTION OF EXEMPLARY EMBODIMENTS

Reference will now be made in detail to the present exemplary embodiments, examples of which are illustrated in the accompanying drawings. Wherever possible, the same reference numbers will be used throughout the drawings to refer to the same or like parts.

The present disclosure provides catheter anchoring devices. The anchoring devices can be used to secure percutaneous catheters or other catheters to a patient. The holders can be used with a wide variety of catheters, including catheters with a wide range of French sizes (e.g., 6F-20F) and/or different types of medical plastic or elastomeric materials. The anchoring devices can be used with a variety of catheter types including, radiology catheters, multi-purpose drainage catheters, percutaneous gastrostomy tubes, and peritoneal lavage catheters.

The catheter anchoring devices can include at least two parts, including an adhesive-backed catheter locking tab and a base portion that engages with the catheter locking tab. As discussed below, the base portion can include an adhesive surface, such that when a catheter is secured to the base portion using the locking tab and base portion configurations described herein, the catheter can be adhesively anchored to the skin of a patient.

Figure 1:
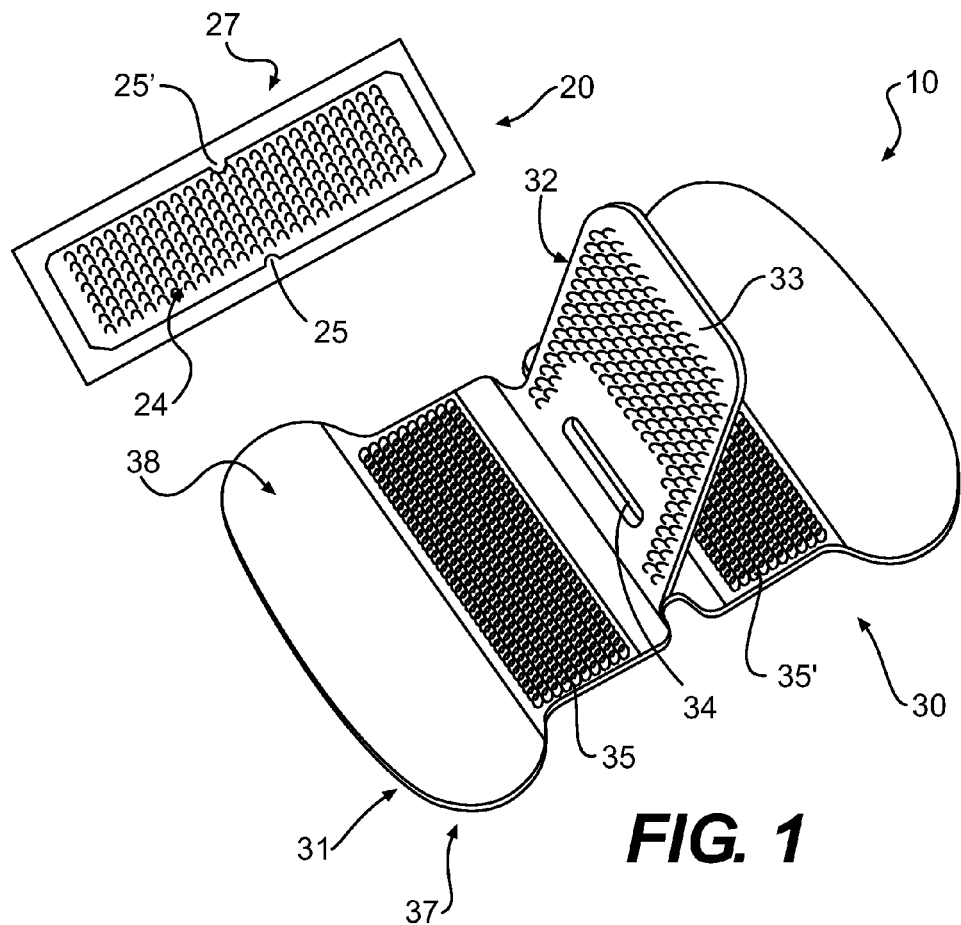
FIG. 1 is a perspective drawing of an anchoring device, according to one embodiment.
Figures 2A, 2B:
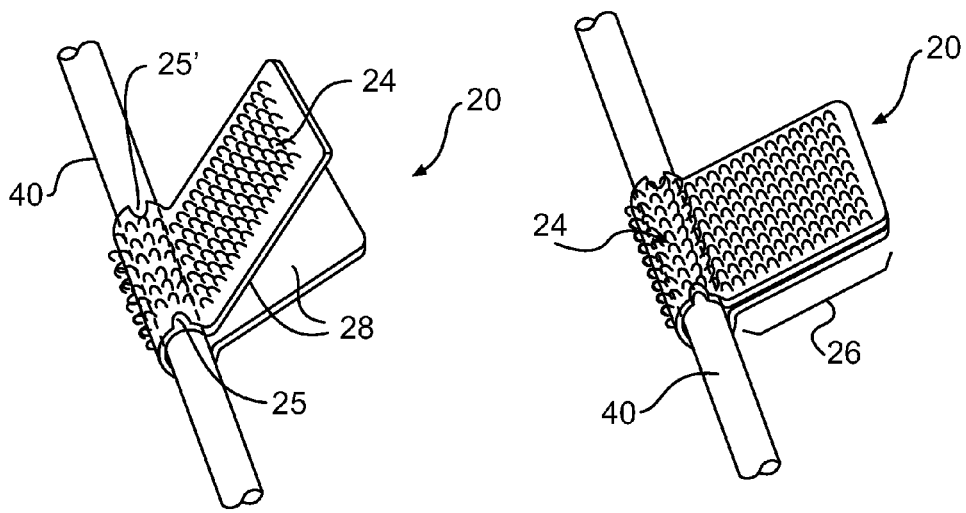
FIG. 2A is a perspective view of an adhesive locking tab of the anchoring device being attached to a catheter, according to one embodiment.
FIG. 2B is a perspective view of an adhesive locking tab of the anchoring device attached to a catheter, according to one embodiment.

FIG. 1 is a perspective drawing of anchoring device 10, according to one embodiment. As shown, the device 10 includes a first adhesive locking tab 20 and a second base portion 30. As discussed further below, the locking tab 20 can be secured to a catheter 40 (as shown in FIGS. 2A-2B). The locking tab 20 and catheter 40 can then be secured to the base portion 30, which can be adhesively secured to a patient's skin to prevent undesirable movement of the catheter 40.

FIG. 2A is a perspective view of the adhesive locking tab 20 of the anchoring device 10 being attached to a catheter 40, and FIG. 2B is a perspective view of the adhesive locking tab 20 attached to the catheter 40. The locking tab 20 can include a front surface 24 including either a hook or a loop type material and a back surface 28 containing an adhesive. In some embodiments, the locking tab 20 also includes a backing 27, which can be removed prior to use to expose the adhesive on the back surface 28. As shown in FIGS. 2A-2B, the locking tab 20 is folded over and adhesively secured around the catheter 40 such that the tab 20 provides a semi-permanent adhesive bond or attachment to the catheter 40. In some embodiments, to visually aid in centering the locking tab around the catheter, the tab 20 has notches 25, 25', or other markings that assist in placement of the tab 20 on a catheter, as shown in FIGS. 1 and 2A. The top surface 24 containing the hook or loop material can surround most or all of a section of the circumference of the catheter 40. As shown, the locking tab 20 can have a size and dimensions such that the back surface 28 of the tab 20 can be adhesively secured to a catheter 40 to form an outwardly extending protrusion 26.

The components 20 and 30 of the anchoring device 10 can be produced from a variety of suitable materials. For example, the locking tab 20 can be made from a low-profile adhesive backed VELCRO® type hook die cut onto a peel back liner. The low-profile hook material is manufactured by 3M as a low-profile hook fastener #7335 made from polyolefin with a very aggressive, high-tack adhesive. The adhesive is a synthetic, rubber-based adhesive that will adhere well to a wide variety of plastic catheter materials such as polyurethane and silicone. In addition, the hook fastener is about 23 mils thick, providing a thin and conformable device.

However, other materials can be used as long as they provide suitable mechanical attachment properties, size, and adhesive ability. In addition, the dimensions of the tab 20 can vary, but generally a reasonable size for the locking tab 20, if formed with a generally rectangular shape, is 0.7 inches wide by about 3 inches long.

As noted, the device 10 also includes a second part base portion 30. The base portion 30 can include a base material layer 31 including a bottom surface 37 for adhesive application to the skin of a patient and a top surface 38 including either a hook or loop type material 35, 35' for engagement with the hook or loop type material 24 of the locking tab 20. The base portion 30 can also include a flexible closure 32 extending from the base material layer 31 and including a hook or loop type material 33 for engagement with the top surface 38 of the base material layer 31. The closure 32 also includes a through-hole 34 sized to allow passage of the tab protrusion 26 when the tab 20 is secured to a catheter 40 to form an insertion interlocking mechanically fixed engagement with the closure 32 when the closure 32 is engaged with the top surface hook or loop material 35 of the base portion 30.

Figure 3:
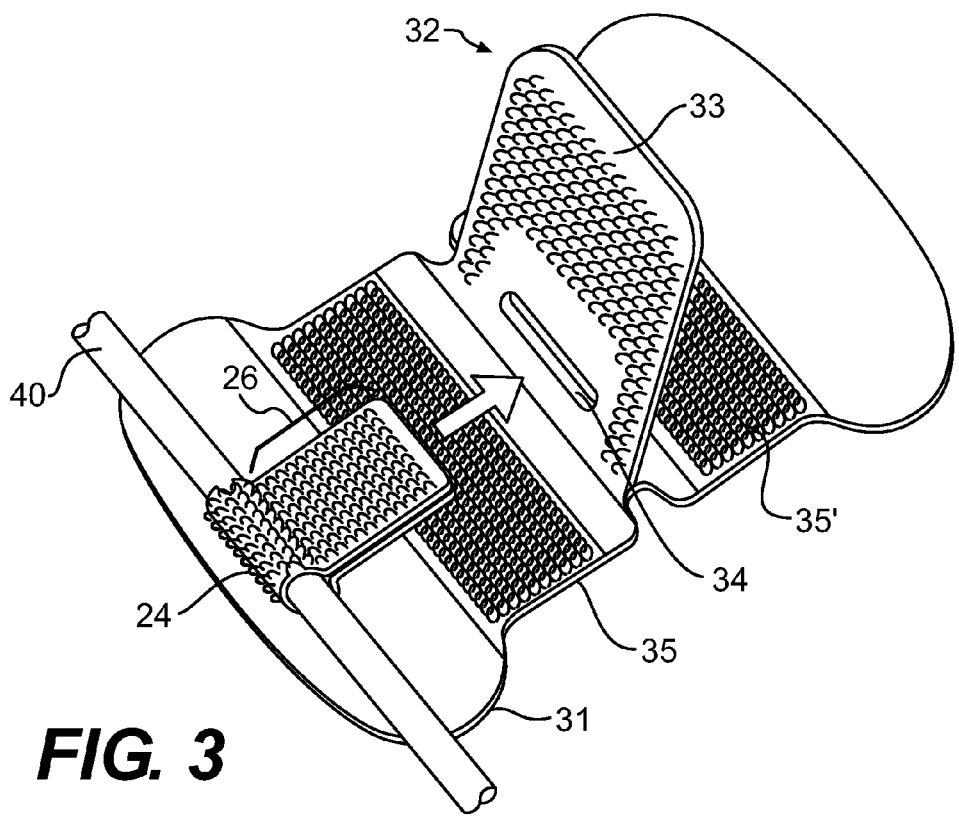
FIG. 3 is a perspective view of a locking tab attached to a catheter being engaged with a base portion of the anchoring device, according to one embodiment.
Figure 4:
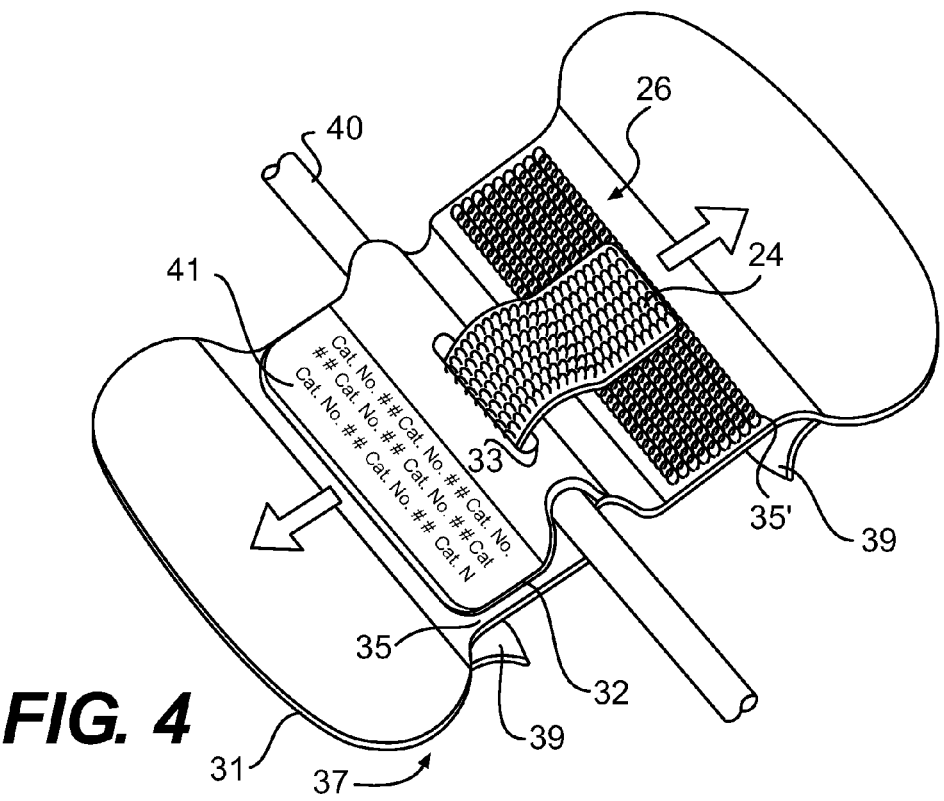
FIG. 4 is a perspective view of the final assembly of the anchoring device secured to a catheter, according to one embodiment.

FIG. 3 is a perspective view of a locking tab 20 attached to a catheter 40 being engaged with a base portion 30 of the anchoring device 10. FIG. 4 is a perspective view of the final assembly of the anchoring device 10 secured to a catheter 40. As discussed above, after the tab portion 20 is joined to a catheter 40, the protrusion 26 of the tab 20 is passed through the opening 34 of the closure 32, and the closure 32 and tab 20 are interlocked and held in place by the interconnection of the hook or loop materials on the tab portion 20, closure 32, and base portion 30, as shown in FIG. 4. In addition, an adhesive layer on the bottom surface 37 of the base portion 30 can be exposed by removal of a covering release liner layer 39, and the assembly can be secured to a patient's skin to prevent undesirable movement of the catheter 40. In this way, the strong adhesive on locking tab 20, along with the interlocked portions of the locking tab 20 and base portion 30 prevent undesired movement of the catheter 40 in any direction (e.g., laterally or forward/backwards).

As shown, the base portion 30, includes hook or loop sections 35, 35' on opposite sides of the closure 32. The sections 35, 35' allow the tab 20, base material layer 31, and closure 32 to interlock with one another. Generally, the closure is centrally located on the base material layer 31, but can be positioned laterally if the anatomic positioning of the device 10 requires an asymmetric shape.

Once engaged the locking tab forms a mechanical interlock engagement with the base portion to positively anchor or fixate the catheter in place to prevent any movement of the catheter in either the forward or rearward direction. In this manner, permanent anchoring or fixation of the catheter is accomplished, which is especially important in a percutaneous catheter whose forward or distal end is often used to drain abscessed internal organs such as in the liver or kidneys. Any disengagement or dislodgement of the catheter would have dire or severe consequences for the patient whether forward, distal, rearward, or proximal. As such, the unique structure of the present invention gives assurance to the clinician that the catheter is truly anchored in place.

The base portion 30, including the base material layer 31, hook or loop materials 35, 35', 33, and closure 32 can be produced from a variety of suitable materials. For example, the base material can be produced using 3M TRANSPORE 1527L or similar materials. In addition, suitable hook and loop type materials can include 3M 7331 white loop with adhesive for securing to the base material, while suitable hook materials can include 3M SJ 3506 white hook with adhesive. Other materials can be used.

Figure 5A:
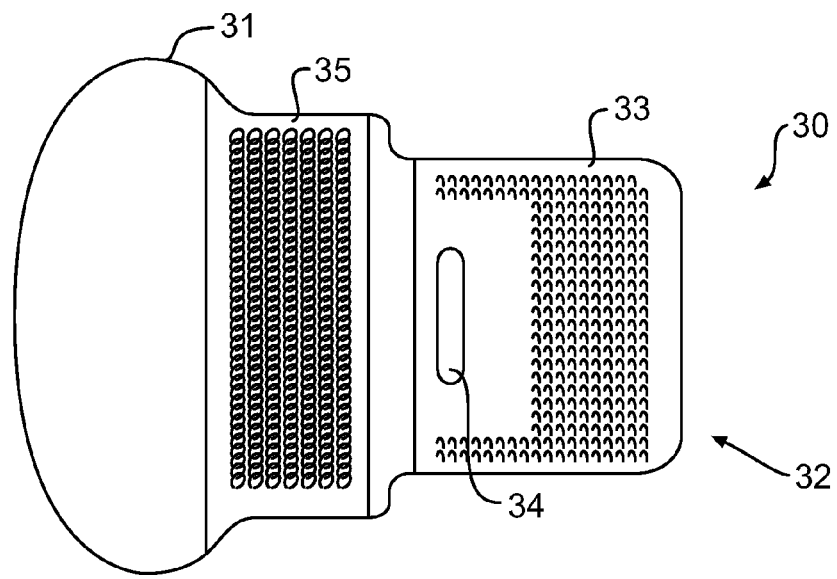
FIGS. 5A-5B are construction drawings depicting the manufacturing assembly of the base portion of the anchoring device, according to one embodiment.
Figure 5B:
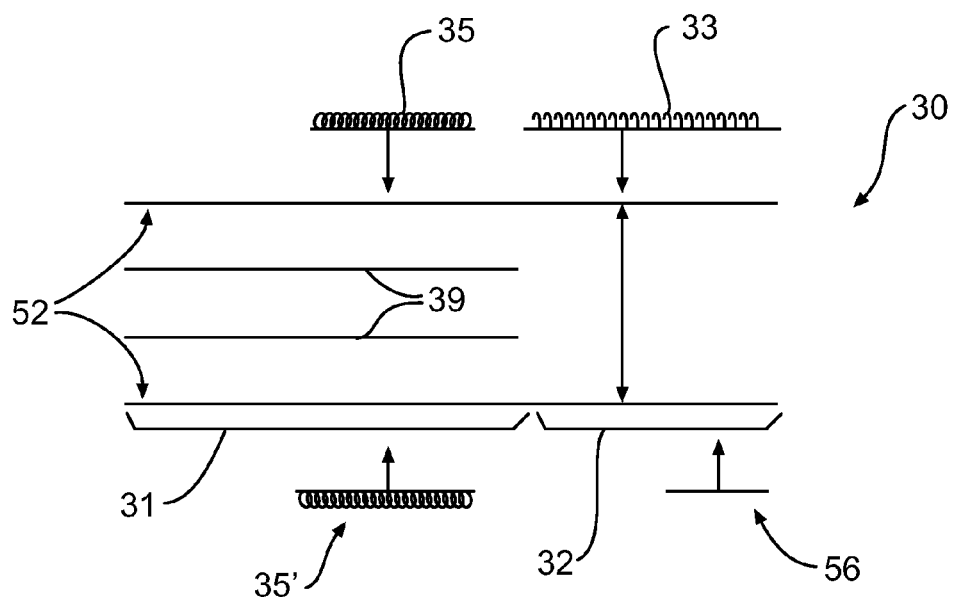

In some embodiments, the base portion 30 with base material layer 31 and closure 32 can be assembled using an automated process. For example, FIGS. 5A and 5B illustrate a process for the continuous, layered automatic construction of the base portion 30. As shown, two layers of material 52 can be used to form portions of the base material layer 31 and closure 32. The material layers 52 can include a medical-grade adhesive tape such as 3M TRANSPORE 1527L or similar material. Along the closure portion 32, the materials are laminated to one another, and within the base material layer portions 31, separate material layers 39 are placed to form the covering release liners 39. The release liners 39 can be made from a material such as silicone-coated Kraft paper, which can be easily removed during use, as shown in FIG. 4. In addition, hook or loop materials 33, 35, 35' are placed on the base layer 31 and closure 32.

In some cases, a continuous adhesive strip 41 (shown in FIG. 4 also) made from a tape, such as 3M-1526 tape, is laminated onto the base portion 30. Adhesive strip 41 can include a randomly repeating pattern printed with any desired graphic information. Spot pad printing of any desired graphic information is also alternately contemplated as well as the continuous adhesive strip 41 with its random repeat pattern printing. After final continuous lamination of the various elements as shown in 5B the final manufacturing step is to die cut the device into its final configuration as shown in 5A.

Figure 5C:
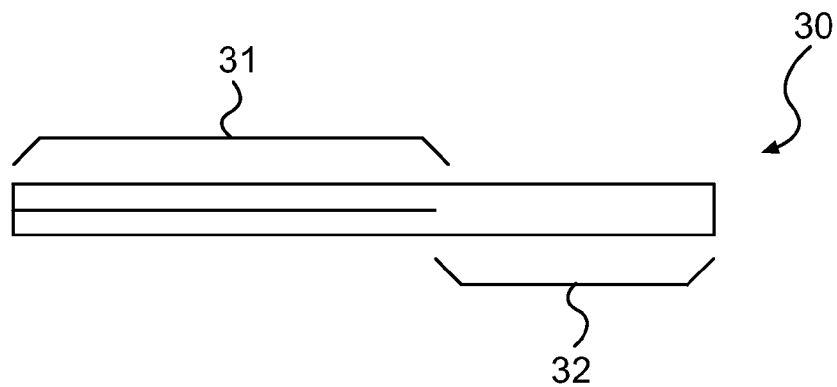
FIGS. 5C-5D are side-end views of the assembly produced according to the process of FIGS. 5A-5B and according to one embodiment.
Figure 5D:
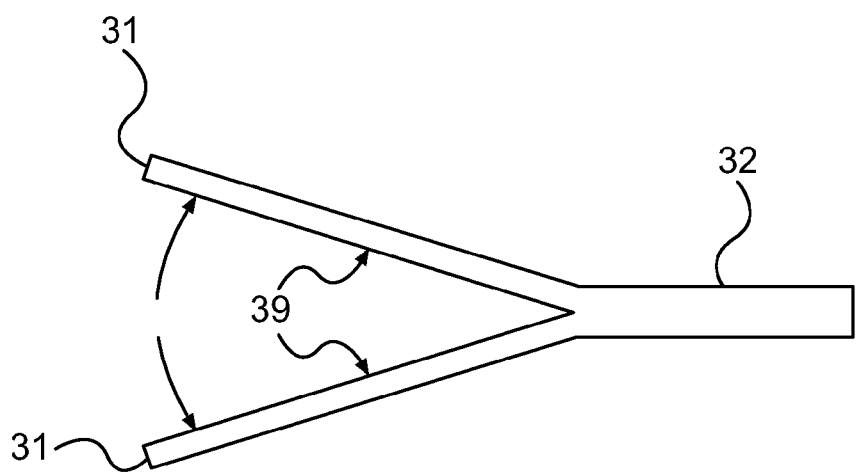

FIGS. 5C-5D are side-end views of the base portion 30 produced according to the process of FIGS. 5A-5B. As shown, the base portion 30 includes the base layer 31 and closure 32. Before use, the portions of the base portion 31 can be spread apart to expose the covering 39 (as shown in FIG. 39) and provide the configuration generally used when interlocking with the locking tab 20, as shown for example in FIGS. 1, 3, and 4).

In some embodiments, instructions for using the assembly can be included on one or more components of the device. For example, instructions for use can be located on the backing 27, coverings 39, or other portions of the device (e.g., on a part of the base layer or closure).

FIGS. 6-9 depict an alternate embodiment of an anchoring device 10'. The device 10' can include a completely circular high profile locking tab 20' having a front surface 24' including hook or loop type material and a back surface 22' containing an adhesive. The device 10' can also include a base portion 30' comprising a base material layer 31 including a bottom surface 37 for adhesive application to the skin of a patient and a top surface 38 including either a hook or loop type material 35 for engagement with the hook or loop type material 24' of the locking tab 20'. The device 10' can also include a flexible closure 32 extending from the base material layer 31 and including a hook or loop type material 33 for engagement with the top surface of the base material layer 38. The closure 32 can also include an enlarged elongated opening 34' sized to allow at least portion of the locking tab 20' to protrude through the opening 34' when the tab 20' is wrapped around a catheter 40 and secured to the top surface of the base material layer 31, as shown in FIGS. 7A-7B.

Figure 8:
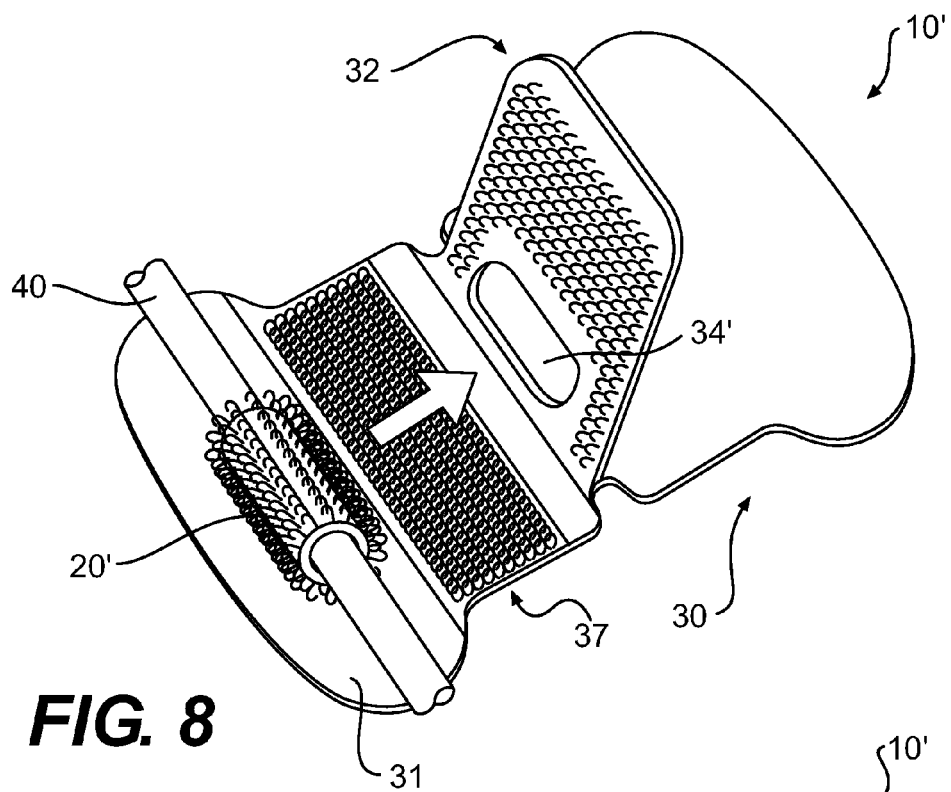
FIG. 8 is a perspective view of a locking tab and catheter during engagement with a base portion of the anchoring device of FIG. 6.
Figure 9:
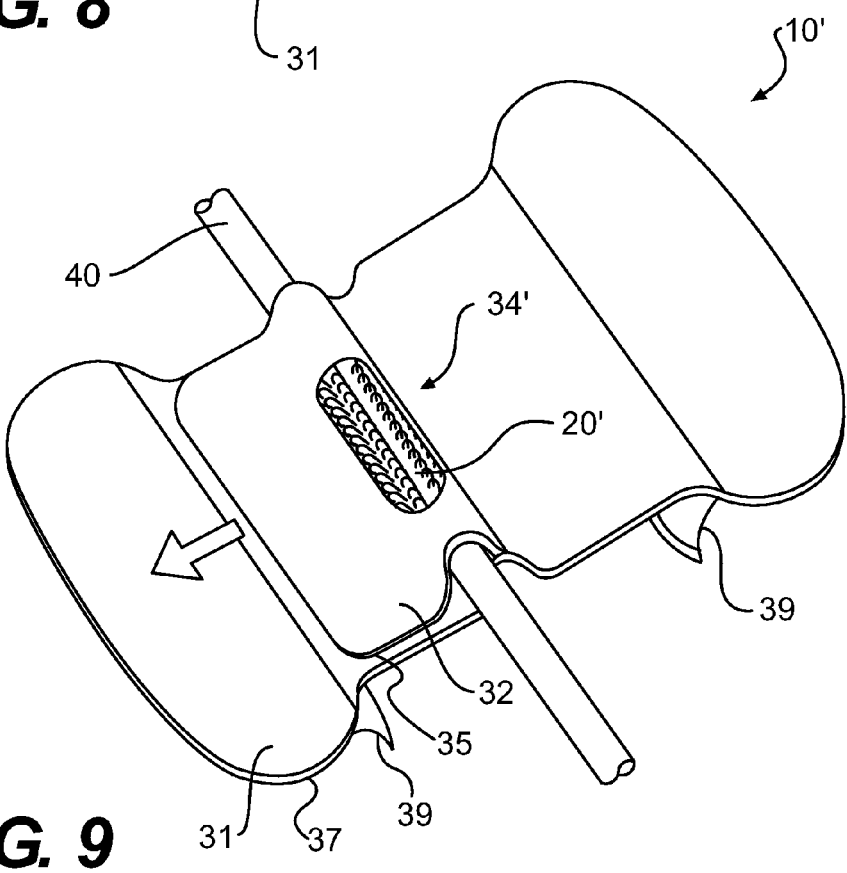
FIG. 9 is a perspective view of the final assembly of the anchoring device of FIG. 6 secured to a catheter, according to one embodiment.

FIG. 8 is a perspective view of a locking tab 20' and catheter 40 during engagement with a base portion of the anchoring device of FIG. 6, and FIG. 9 is a perspective view of the final assembly of the anchoring device of FIG. 6 secured to catheter 40. As with the other embodiment, the catheter 40 and attached locking tab 20' are placed on the base material layer 31, and the closure 32 is folded over the locking tab 20', such that the hook and loop materials of the locking tab 20', base material layer 31, and closure 32 secure the components to one another. In addition, the bottom surface 37 of the base portion can include an adhesive to secure the device and catheter in place. The adhesive can be exposed prior to use by removal of covering layers 39, which can be peeled from the bottom surface 37.

The materials used to form the components of the device of FIGS. 6-9 can be the same or similar to those used to produce the devices described with respect to FIGS. 1-5. However, in some embodiment, it may be desirable to use a high-profile hook material for the locking tab 20'. For example, a suitable material can include a high-profile, adhesive-backed nylon hook material about 0.075 inches in thickness.

In addition, the opening 34' on the closure 33 can be larger to allow the locking tab to at least partially protrude through the opening 34'. In that case, the locking tab protrusion is inserted through the enlarged closure opening 34', which provides an interlocking engagement with the closure to anchor the catheter in place and prevent forward or rearward movement. Various types of locking tab can be used to anchor the catheter so long as there is provided some type of locking tab extension or outward protrusion that can be partially or fully inserted into the flexible closure opening. As such, the locking tab protrusion can take many forms or configurations, while still remaining within the confines of the underlying function of an interlocking engagement between the catheter locking tab and the closure.

Figure 10:
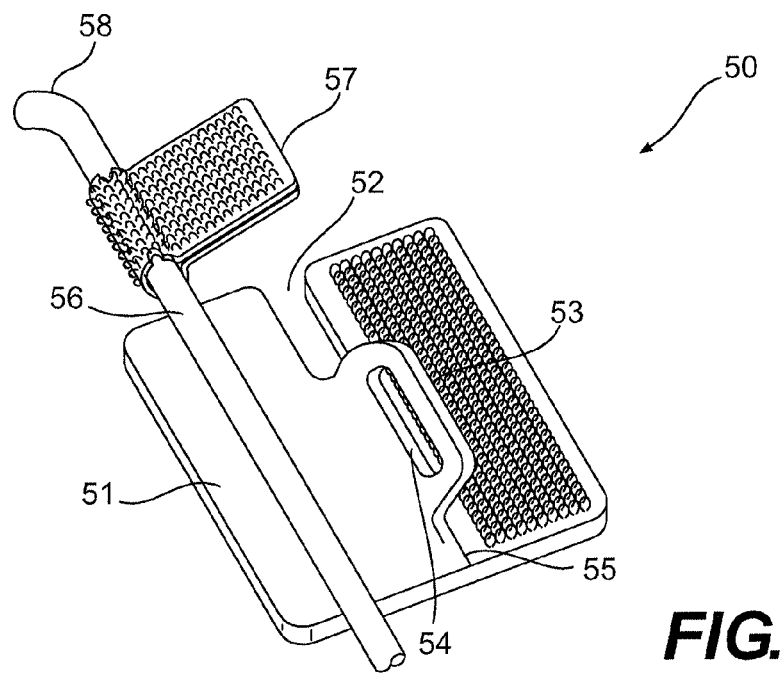
FIG. 10 is a perspective view of another embodiment having a flexible injection molded base portion.

FIG. 10 is a perspective view of an alternate embodiment 50 having a flexible injection molded base portion 51. In some embodiments, base portion 51 is about 2 inches by 2 inch square. Base portion 51 can be molded of a flexible yet strong polyurethane material with about 50 Shore A durometer and having a typical wall thickness of about 0.050 inches in thickness. In the embodiment shown in FIG. 10, base portion 51 has a catheter retention slot 52 molded in as part of the base 51 that butts up against upright extension portion 53 having built in through hole slot 54. On one side of base portion 51 is VELCRO® loop platform 55, which is laminated onto the base portion 51. The catheter 56 with adhesively attached hook can have a similar or the same structure as depicted in FIG. 2B. In some embodiments, adhesive backed tab portion 57 is adhered only about 1 inch back from skin catheter exit site 58.

Figure 11:
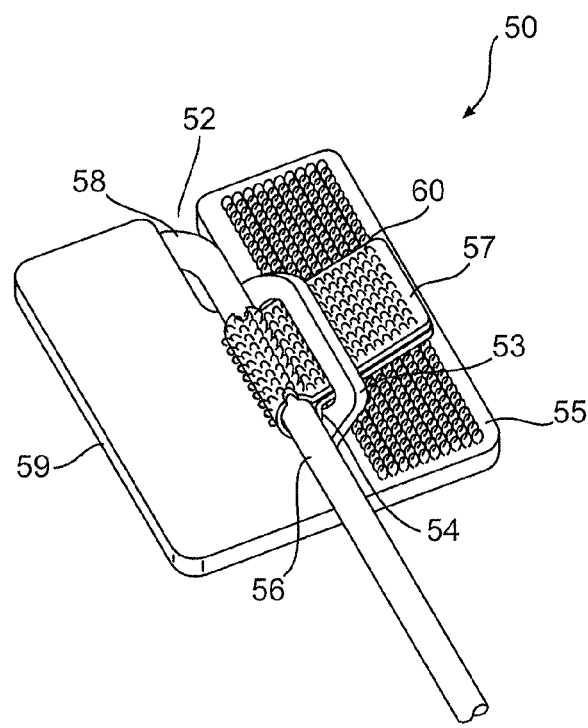
FIG. 11 is a perspective view of the anchoring device of FIG. 10, in accordance with some embodiments.

FIG. 11 is a perspective view of anchoring device 50 of FIG. 10, in accordance with some embodiments. In FIG. 11, the device is adhesively secured to a patient's skin by base portion adhesive 59. As can be seen, tab portion 57 is inserted through slot 54 on upright extension portion 53 and tab portion 57 with VELCRO® hooks 60 is pressed onto VELCRO® loop platform 55 to mechanically form an interlocking engagement with the top loop platform surface 55. As such, the catheter 56 with hook is mechanically locked in place such that the catheter cannot move from exit site 58. This provides a unique ultra secure fixation of the catheter to prevent any inward or outward migration or movement of the catheter, such that base portion 51 acts as an external bolster to prevent catheter migration. Such secure fixation is important for percutaneous catheters used to drain or treat visceral abscesses (e.g., on kidneys or the liver).

Figure 12:
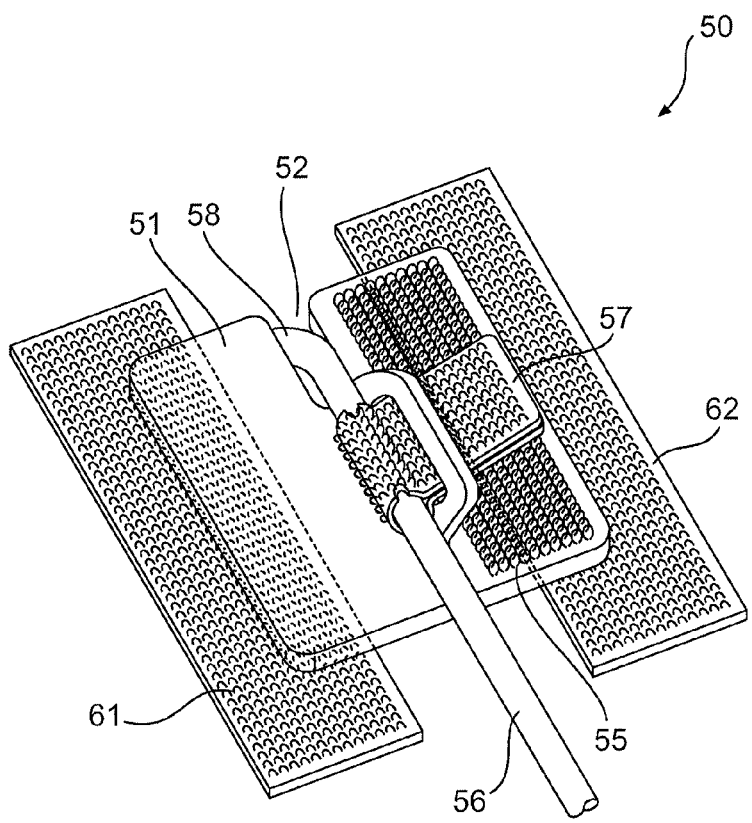
FIG. 12 is a perspective view of an anchoring device wherein the base portion is secured by two tape strips, in accordance with some embodiments.

FIG. 12 is a perspective view of anchoring device 50 wherein the base portion 51 is secured by two tape strips 61 and 62, in accordance with some embodiments. Tape strips 61 and 62 can be formed of various types of medical tapes. In some embodiments, as shown in FIG. 12, perforated breathable transparent tapes known as Transpore® are used for tape portions 61 and 62. In some embodiments, tape strips 61 and 62 can be removed and the base portion 51 can be slightly lifted for visualization and viewing and/or treatment of the skin exit site 58. Base portion 51 can be molded from clear, lightweight, flexible and conformable transparent polyurethane or DEHP free PVC for viewing through the base portion 51 directly onto the skin surface. Further, in some embodiments, side strips 61 and 62 can be easily removed, such that base 51 or catheter 56 can be repositioned, if desired, and then new side strips 61 and 62 can be reapplied to secure base 51 and catheter 56 in a new position.

While the enlarged slot or hole located in the closure, as shown in FIG. 6, is shown as an enlarged oval, various embodiments utilize various sizes or configurations of slot or hole, such that the slot or hole permits the insertion of the locking tab on the catheter to enter any configured hole or slot on the closure. Likewise, in various embodiments, different styles or types of catheter locking tabs can be designed without departing from the underlying anchoring devices described herein. In addition, the hook and loop on the tab, base, and closure can be exchanged or reversed by having loop on the closure and hook on the base tape portion without impacting the functionality of the devices. Further, in some embodiments, other types of mechanical engagement mechanisms are used in place of some or all of the hook or loop materials.

In some cases, the devices described herein are made for single use, and the devices are discarded when not needed, or replaced if they become worn or unsanitary. In some cases, individual parts of the devices may be replaced. For example, for longer term use, the skin adherent base portion can be replaced after being used for a week or so, while the catheter locking tab remains attached to the catheter.

Other embodiments will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A catheter anchoring device, comprising:
a locking tab having a front surface including a first mechanical engagement material and a back surface containing an adhesive, the locking tab having a size and dimensions such that the back surface of the tab can be adhesively secured to a catheter by wrapping the back surface around a catheter surface such that that the locking tab forms an outwardly extending protrusion from the catheter; and
a base portion comprising:
a base material layer including a bottom surface for adhesive application to the skin of a patient and a top surface including a second mechanical engagement material for engagement with the first mechanical engagement material of the locking tab; and
an extension portion extending from the base material layer and having a through-hole sized to allow passage of the tab protrusion when the tab is secured to a catheter to form an interlocking engagement with the extension portion.

2. The device of claim 1, wherein the extension portion is a flexible closure further including a third mechanical engagement material for engagement with the top surface of the base material layer, and wherein the tab protrusion forms an interlocking engagement with the flexible closure when the closure is engaged with the top surface of the base portion.

3. The device of claim 2, wherein the first and third mechanical engagement materials are hook type materials and the second mechanical engagement material is a loop type material, or the first and third mechanical engagement materials are loop type materials and the second mechanical engagement material is a hook type material.

4. The device of claim 1, wherein the locking tab has a substantially rectangular shape.

5. The device of claim 1, wherein the through-hole is an elongated hole.

6. The device of claim 1, wherein the extension portion extends from a center region of the top surface of the base material layer and the top surface includes the second mechanical engagement material on both sides of the extension portion.

7. The device of claim 1 wherein the base portion is a molded component.

8. The device of claim 1 wherein the bottom surface is adhesively secured to the top surface.

9. The device of claim 1, further including a catheter secured to the locking tab.

10. A catheter anchoring device, comprising:
a locking tab having a front surface including a first mechanical engagement material and a back surface containing an adhesive; and
a base portion comprising:
a base material layer including a bottom surface for adhesive application to the skin of a patient and a top surface including a second mechanical engagement material for engagement with the first mechanical engagement material of the locking tab; and
an extension portion extending from the base material layer and having an elongated opening sized to allow at least a portion of the locking tab to protrude through the opening when the tab is wrapped around a catheter body and secured to the top surface of the base material layer.

11. The device of claim 10, wherein the extension portion is a flexible closure further including a third mechanical engagement material for engagement with the top surface of the base material layer.

12. The device of claim 11, wherein the first and third mechanical engagement materials are hook type materials and the second mechanical engagement material is a loop type material, or the first and third mechanical engagement materials are loop type materials and the second mechanical engagement material is a hook type material.

13. The device of claim 10, wherein the locking tab has a substantially rectangular shape.

14. The device of claim 10, wherein the extension portion extends from a center region of the top surface of the material the top surface includes hook or loop material on both sides of the extension portion.

15. The device of claim 10, further including a catheter secured to the locking tab.

16. A method for securing a catheter using a catheter anchoring device, the method comprising:
securing a catheter to a locking tab of the catheter anchoring device having a front surface including a first mechanical engagement material and a back surface containing an adhesive, by adhesively securing the locking tab to the catheter by wrapping the back surface around a catheter surface such that that the locking tab forms an outwardly extending protrusion from the catheter; and securing the locking tab attached to the catheter to a base portion of the catheter anchoring device, wherein the base portion comprises a base material layer including a bottom surface that is adhesively applied to the skin of a patient and a top surface that includes a second mechanical engagement material, and the base portion further comprises a extension portion extending from the base material layer and including a through-hole, the securing comprising:
- engaging the first mechanical engagement material of the locking tab with the second mechanical engagement material of the top surface,
- passing the tab protrusion through the through-hole to form an interlocking engagement with the extension portion, and
- engaging the locking tab with the second mechanical engagement material of the top surface.

17. The method of claim 16, wherein the extension portion is a flexible closure further including a third mechanical engagement material for engagement with the top surface of the base material layer, and wherein the method further includes engaging the flexible closure with the top surface of the base portion.

18. The method of claim 17, wherein the first and third mechanical engagement materials are hook type materials and the second mechanical engagement material is a loop type material, or the first and third mechanical engagement materials are loop type materials and the second mechanical engagement material is a hook type material.

19. The method of claim 16, wherein the locking tab has a substantially rectangular shape.

20. The method of claim 16, wherein the through-hole is an elongated hole.

21. The method of claim 16, wherein the flexible closure extends from a center region of the top surface of the base material layer and the top surface includes the second mechanical engagement material on both sides of the flexible closure.

\* \* \* \* \*